(12) United States Patent
Hackel

(10) Patent No.: US 10,390,906 B2
(45) Date of Patent: Aug. 27, 2019

(54) MEDICAL LUMINAIRE

(71) Applicant: KALTENBACH & VOIGT GMBH, Biberach (DE)

(72) Inventor: André Hackel, Biberach (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 0 days.

(21) Appl. No.: 14/682,990

(22) Filed: Apr. 9, 2015

(65) Prior Publication Data

US 2015/0292684 A1 Oct. 15, 2015

(30) Foreign Application Priority Data

Apr. 14, 2014 (EP) ..................... 14164616

(51) Int. Cl.
| | |
|---|---|
| *A61C 1/08* | (2006.01) |
| *F21K 99/00* | (2016.01) |
| *A61B 50/28* | (2016.01) |
| *A61B 90/35* | (2016.01) |
| *F21V 5/00* | (2018.01) |
| *A61B 90/30* | (2016.01) |
| *F21V 3/00* | (2015.01) |
| *F21W 131/202* | (2006.01) |
| *F21Y 115/10* | (2016.01) |

(52) U.S. Cl.
CPC .............. *A61C 1/088* (2013.01); *A61B 50/28* (2016.02); *A61B 90/30* (2016.02); *A61B 90/35* (2016.02); *F21V 5/003* (2013.01); *A61B 2090/309* (2016.02); *F21V 3/00* (2013.01); *F21W 2131/202* (2013.01); *F21Y 2115/10* (2016.08)

(58) Field of Classification Search
CPC ........... A61C 1/088; F21V 5/003; F21V 3/00; F21W 2131/202; F21W 2131/205; F21W 2131/20; F21W 2131/402; A61B 90/30; A61B 2090/309
USPC ..... 362/804, 33, 239, 249.1, 8, 249.09, 572, 362/269
See application file for complete search history.

(56) References Cited

U.S. PATENT DOCUMENTS

| | | | | |
|---|---|---|---|---|
| 3,887,801 | A * | 6/1975 | Ilzig ........................ | F21V 17/02 362/233 |
| 5,174,649 | A * | 12/1992 | Alston ...................... | F21V 5/04 362/244 |
| 6,478,453 | B2 * | 11/2002 | Lammers ................ | F21S 6/002 353/23 |

(Continued)

FOREIGN PATENT DOCUMENTS

| | | |
|---|---|---|
| DE | 10 2011 075 753 A1 | 6/2012 |
| EP | 2 469 159 A2 | 6/2012 |

OTHER PUBLICATIONS

European Search Report and Opinion, received in European Patent Application No. 14164616.6, dated Sep. 30, 2014 (5 pages).

*Primary Examiner* — Anh T Mai
*Assistant Examiner* — Arman B Fallahkhair
(74) *Attorney, Agent, or Firm* — Michael Best & Friedrich LLP

(57) ABSTRACT

A medical luminaire, for example a dental treatment luminaire for the intraoral illumination of a surgical field, has at least one illuminating unit with light-producing means and with optical means for generating a field of light in an object plane, wherein a diffuser is provided that is designed to widen the field of light in the object plane.

13 Claims, 3 Drawing Sheets

(56) References Cited

U.S. PATENT DOCUMENTS

| | | | |
|---|---|---|---|
| 6,606,173 B2* | 8/2003 | Kappel | H04N 5/7441 |
| | | | 348/E5.141 |
| 7,167,308 B1* | 1/2007 | Krishnamurthy | G02B 3/08 |
| | | | 359/457 |
| 7,878,683 B2* | 2/2011 | Logan | F21V 5/00 |
| | | | 362/249.02 |
| 7,980,738 B2* | 7/2011 | Chiang | F21V 14/02 |
| | | | 362/427 |
| 8,197,103 B2* | 6/2012 | Chang | G02B 5/0215 |
| | | | 362/244 |
| 8,454,197 B2* | 6/2013 | Hauschulte | F21S 2/005 |
| | | | 362/239 |
| 8,632,189 B2* | 1/2014 | Read | G03B 35/20 |
| | | | 353/7 |
| 8,816,599 B2* | 8/2014 | Wood | F21S 6/00 |
| | | | 315/291 |
| 9,016,916 B2* | 4/2015 | Marka | A61B 19/5202 |
| | | | 362/572 |
| 9,119,668 B2* | 9/2015 | Marka | A61B 90/35 |
| 9,217,550 B2* | 12/2015 | Kim | F21V 3/0445 |
| 2006/0193578 A1* | 8/2006 | Ouderkirk | B29C 47/0004 |
| | | | 385/115 |
| 2011/0001431 A1 | 1/2011 | Brukilacchio | |
| 2011/0175551 A1 | 7/2011 | Wood et al. | |
| 2011/0228534 A1* | 9/2011 | Zhang | F21S 6/002 |
| | | | 362/240 |
| 2012/0243666 A1 | 9/2012 | Lenchig, Jr. | |

\* cited by examiner

MEDICAL LUMINAIRE

BACKGROUND

Embodiments of the invention relate to a medical luminaire. More particularly, embodiments of the invention relate to a dental treatment luminaire for the intraoral illumination of a surgical field that has at least one illuminating unit with light-producing means and with optical means for generating a field of light in an object plane.

A luminaire conforming to this type is known from, for example, DE 10 2011 075 753 A1, pertaining to the applicant. In the case of the luminaire described therein, LEDs or LED arrays find application as light-producing means, to which various optical means are assigned, in order ultimately to ensure an illumination of the surgical field that is suitable for treatment purposes. These optical means comprise, for example, firstly a collimator for beam focusing and also a so-called condenser arranged downstream in the light path, with the aid of which the light beams are deflected and/or mixed in such a manner that the field of light being striven for is achieved in an object plane. As a rule, in addition to these optical means a cover plate has also been provided in the beam path, the function of which, however, consists primarily in protecting the optical and electronic components of the luminaire—that is to say, in particular, the light-producing means and also the optical units described above—against contamination and damage.

From the state of the art described above it is moreover already known to employ several illuminating units of such a type within a medical luminaire, which are arranged at varying angles and oriented in such a manner that the overall field of illumination results from the superposition of several individual illuminated fields, having the consequence that the formation of shadows, for example by the treating dentist, is minimised. Ideally, in this connection the illuminating units are oriented in such a manner and designed in such a manner that the individual fields of light are substantially identical—that is to say, they overlap completely.

The field of light ultimately generated should in this case be illuminated as homogeneously as possible, in order, also in the event of possible slight movements of the head of the patient, still to obtain a well-illuminated treatment field. In this way the situation can be avoided where, in the event of slight movements of the head of the patient, the dentist has to reposition the field of illumination each time by appropriate adjusting of the luminaire. The size of the treatment field to be illuminated in this case is limited by the specification of standard ISO968, which requires a maximal illuminance of 1200 lux at a spacing of 60 mm above the centre. The background for this regulation is that the patient is not to be dazzled unnecessarily.

SUMMARY

In the case of the luminaire known from the state of the art, compliance with the aforementioned dazzling limit in conjunction with a large, homogeneously illuminated field of light is ensured with the aid of the optical elements finding application. In the marginal region of the field of light a transition arises in this case from a region of high light intensity of about 20 klux to a region of low light intensity of, for example, 2 klux over a very short distance. In this connection it has become evident that such a high so-called brightness gradient can have a fatiguing effect on the activity of the eyes of the dentist.

Another problematical aspect consists furthermore in the fact that, with the projected superposition of the fields of illumination of the individual illuminating units so as to yield the overall field of illumination in the object plane, an offset, by reason of manufacturing inaccuracies that cannot be avoided completely, may arise between the individual fields of illumination. An offset of such a type, even if it is only slight, is perceived by the dentist, specifically in such a manner that he/she no longer experiences the overall field of illumination as a uniformly illuminated surface.

Proceeding from this state of the art, one object of certain embodiments of the invention is therefore to improve the configuration of a medical luminaire in such a manner that a better and more agreeable illumination of the surgical field can be achieved.

The object is achieved in some embodiments by a medical luminaire for intraoral illumination of a surgical field. The medical luminaire includes at least one LED and at least one lens configured to generate a field of light in an object plane. The medical luminaire further includes a diffuser configured to widen the field of light in the object plane.

With a view to avoiding the problems described above, the solution according to certain embodiments of the invention provides for integrating into the beam path of the illuminating unit a diffuser that diminishes the large gradient from the field of illumination to the unilluminated surroundings. The perceived offset of individual fields of illumination is lessened with the aid of the diffuser, resulting in a more homogeneous, more uniform brightness distribution in the field of illumination. At the same time, strong contrasts in the marginal region of the field of illumination are avoided, leading ultimately to a distinctly more agreeable illumination of the surgical field.

According to some embodiments of the invention, a medical luminaire, for example a dental treatment luminaire for the intraoral illumination of a surgical field, is accordingly proposed that has at least one illuminating unit with light-producing means and also with optical means for generating a field of light in an object plane, wherein a diffuser is provided that is designed to widen the field of light in the object plane.

There are various possibilities for realising the diffuser according to embodiments of the invention. In this connection the use of a diffuser having a holographic structure (for example, a so-called µ-structure) has proved particularly advantageous, which leads to a circularly or elliptically polarised light and at the same time has a high transmission. With the aid of a diffuser of such a type, not only can the aforementioned problems be avoided by widening the field of light in the object plane, but said diffuser furthermore also affords the advantage that a distinctly lesser dazzling of the physician exists, since reflections, for example on the dental surfaces of a patient, are avoided.

By way of diffuser, use may then be made of, for example, a film or a rigid filter which is integrated into the optical beam path of the illuminating unit. As an alternative to the use of a separate element as a diffuser, however, it would also be conceivable, for example, to form the µ-structure on an optically active surface of the optical means of the illuminating unit which are already present, or on a cover plate of the luminaire. As a rule, in the case of these components it is a question of plastic elements that are produced in an injection-moulding process, i.e. the structure of the diffuser is then integrated in straightforward manner into the appropriate injection-moulding tool, ultimately having the result that the diffuser can be produced very economically and can be integrated into the luminaire.

A further advantage of the integration of the diffuser into the injection-moulding tool for producing one of the optical components or the cover consists in the fact that the degree of scattering or the degree of circulation of the light can be created in location-dependent manner. By this means, the gradient of the transition of the field of illumination to the surroundings can again be influenced better and can be set in system-specific manner. Another conceivable possibility would also consist in generating the diffuser with the aid of a suitable eroding structure on an optically active surface in the beam path of the luminaire.

As already mentioned, the medical luminaire according to embodiments of the invention preferably has several illuminating units that are oriented and designed in such a manner that the corresponding fields of light in the object plane substantially coincide. In this case there may be provision, in particular, that a common diffuser for all the illuminating units is employed, which can then be realised in very simple manner by the structure of the diffuser being a constituent of a common cover of the luminaire. In one embodiment, the invention provides.

BRIEF DESCRIPTION OF THE DRAWINGS

In the following the invention will be elucidated in more detail with reference to the enclosed drawing. Shown are.

DETAILED DESCRIPTION

Figure 1:
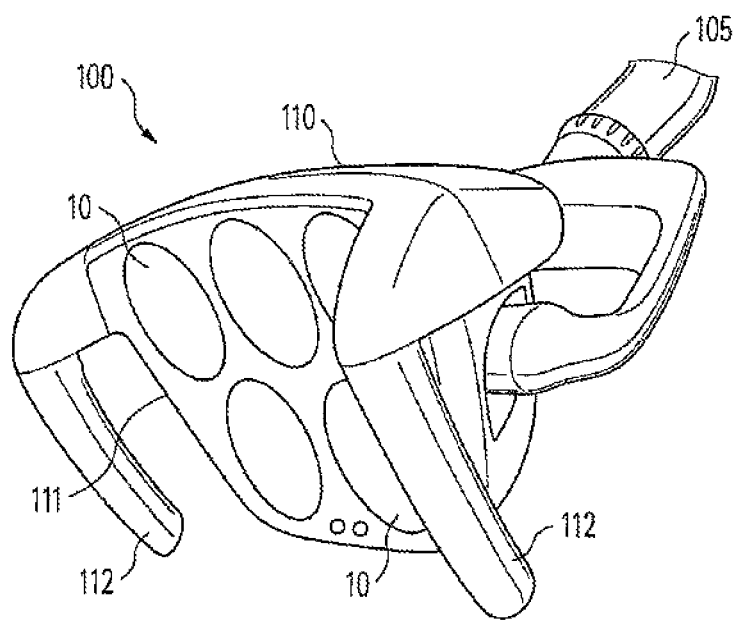
FIG. 1 is a perspective view of a dental treatment luminaire according to one embodiment of the invention.

The medical luminaire represented in a perspective view in FIG. 1 and provided generally with reference symbol 100 is a dental treatment luminaire, with the aid of which the surgical field of a dentist's workstation is to be illuminated. The luminaire head 110 is adjustably arranged on an articulated arm 105, which has not been represented in any detail, in such a manner that it can be oriented towards the surgical region in the desired way. With a view to better adjustability, for this purpose the housing 111 of the luminaire head has two lateral gripping portions 112 which enable a simple manual adjustment of the arrangement of the luminaire 100.

The generation of light and emission of light in the case of the luminaire 100 according to FIG. 1 are effected with the aid of several illuminating units 10 which each generate a bundle of rays which is emitted via an anterior transparent light-radiating side of the luminaire 100. In the embodiment represented, five illuminating units 10 are provided, three of these having been arranged in an upper row, and two below them, in such a manner that, seen overall, a slightly trapezoidal light-radiating surface arises. However, other arrangements are also known, in which, for example, four or five illuminating units are arranged alongside one another.

Figure 2:
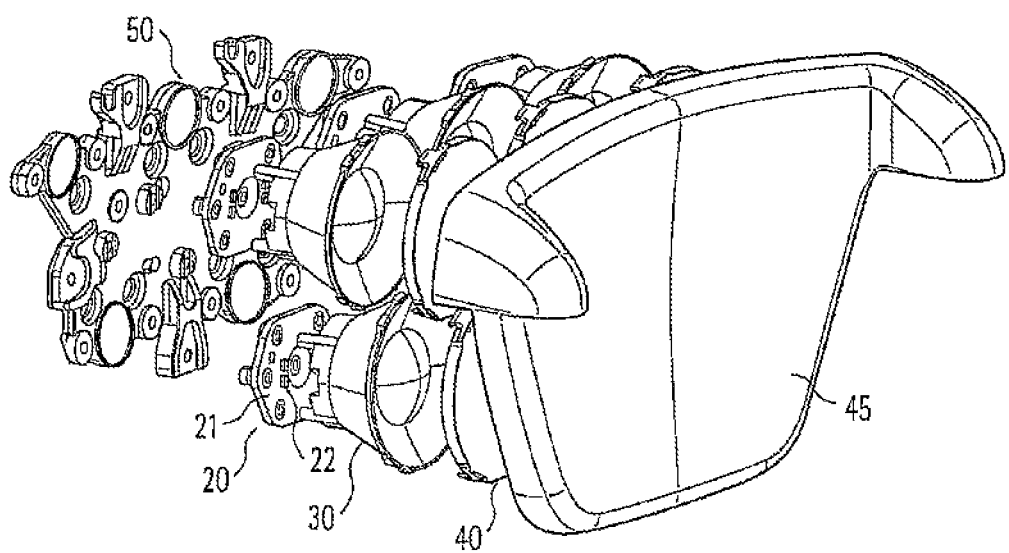
FIG. 2 is an exploded view of the components of the luminaire according to FIG. 1 that are responsible for the generation of the field of light.

The components of the luminaire 100 that are essential for the generation of light and emission of light are shown in FIG. 2 in an exploded representation. In this case a pcb or printed circuit board arranged in the housing 111 serves as carrier element 50, on which the individual illuminating units 10 are mounted. These illuminating units 10 consist, in the embodiment represented, of three essential components, namely the light-producing means 20, first optical means for beam formation 30, and also second optical means for generating an illuminated field 40. The actual emission of light is then effected via a light-transmitting cover plate 45 which covers the anterior light-radiating region of the luminaire head 110 and at the same time also constitutes a protection for the components located inside.

The structure and the mode of operation of the various components of the illuminating units 10 correspond substantially to the structure known from DE 10 2011 075 753 A1, already mentioned. Accordingly, in the following the function of the various components will be elucidated only briefly.

Reference symbol 20 denotes the light-producing means, as already mentioned, which, in the case represented, are constituted by LED light-sources. Strictly speaking, one or more LEDs 22 which are responsible for the generation of light are arranged in each instance on a carrier element in the form of an approximately hexagonal carrier plate 21. As already mentioned, it may be a question of individual LEDs or of LED arrays, in which connection it would be entirely conceivable to combine different LEDs with one another. In this case it might be a question of LEDs of differing colour or colour temperature, the light thereof then being mixed by the optical means, described in still more detail in the following, in such a manner that ultimately the emission of light of the luminaire 100 is effected with light of the desired hue or having the desired colour temperature. The carrier elements 21 for the LED light-sources 22 have in this case been coupled with the carrier 50, whereby, for example, special measures may have been provided, by which an efficient dissipation of the heat arising during operation is guaranteed.

Then, first of all, the first optical means 30 are arranged in the beam path of the light generated by the LED light-sources 22. These are means for collimating the LED light, with the aid of which the light ordinarily radiated by the LED light-producing means 22 within a very large angular range is accordingly firstly focused. These optical means 30 for beam focusing can be realised in the most diverse ways and, for example, may comprise, as known from the state of the art, reflector elements and lens elements. What is essential is that with the aid of these first optical means 30 the light is brought together into a relatively narrow bundle of rays which then impinges on the second optical means 40.

These second optical means 40 are decisively responsible for achieving the field of light being striven for in the object plane. That is to say, these second optical means 40 deflect the light rays of the bundle of rays generated by the first optical means 30 in such a manner that the light is directed as uniformly as possible onto a defined region which then constitutes the so-called illuminated field. In accordance with DE 10 2011 075 753 A1, described above, a conceivable configuration of these second optical means may consist for example, in these being constituted by a disc which has a plurality of lens-like elements. In this case the lenses are configured in such a manner that they themselves deflect the correspondingly incident partial-beam bundle in such a manner that the field of light is generated. That is to say, by each individual lens a stand-alone virtual light-source, so to speak, is formed which illuminates the desired region. In this case the individual lenses may, for example, then be fashioned in such a manner that all the virtual light-sources formed by this means illuminate an identical region, so that accordingly an illumination that is as uniform as possible is achieved by superposition of a plurality of individual bundles of rays. Furthermore, with this type of illumination of a common region by a plurality of individual virtual light-sources a formation of shadows can be reduced. As already mentioned, however, the second optical means 40 might also be fashioned otherwise, so that, for example, the virtual light-sources generate bundles of rays overlapping in offset manner, which then, however, again jointly illuminate the field of light. Furthermore, it would also be conceivable to bring together the first and second optical means 30 and 40 in a common structural unit.

The superposing of individual bundles of rays is effected, incidentally, not only with regard to the mode of action of the second optical means 40 but, for example, also with respect to the various illuminating units 10. This is represented, first of all, in FIGS. 3 and 4 with reference to the luminaire known from the state of the art, whereby in FIG. 13 the superposition of the bundles of rays of two illuminating units 10 arranged one above the other is shown in lateral representation. It can be discerned here that the light is firstly transformed by the first optical means 30 in each instance into an almost parallel bundle of rays. The second optical means 40, however, then widen the respective bundle of rays, the arrangement and orientation of the various optical components of the two illuminating units 10 being such that both bundles of rays I and II ultimately emitted are substantially identically superposed in an object plane 200. By this means, the schematically indicated field of light 250 is defined which characterises the total emission of light of the luminaire 100.

Figure 3:
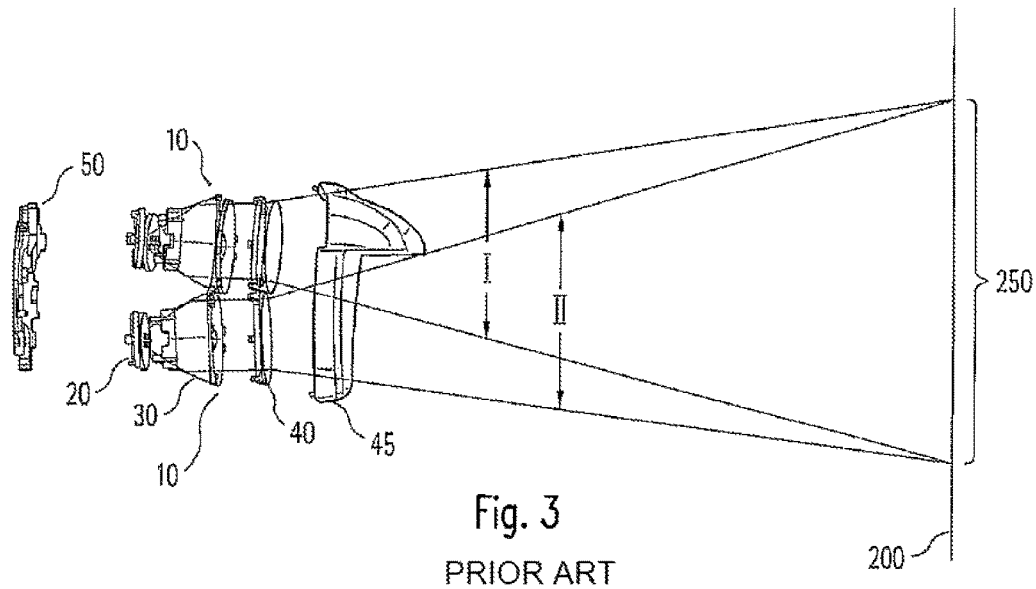
FIGS. 3 and 4 are schematic representations relating to the mode of action of the optical components in the case of a luminaire according to the state of the art.
Figure 4:
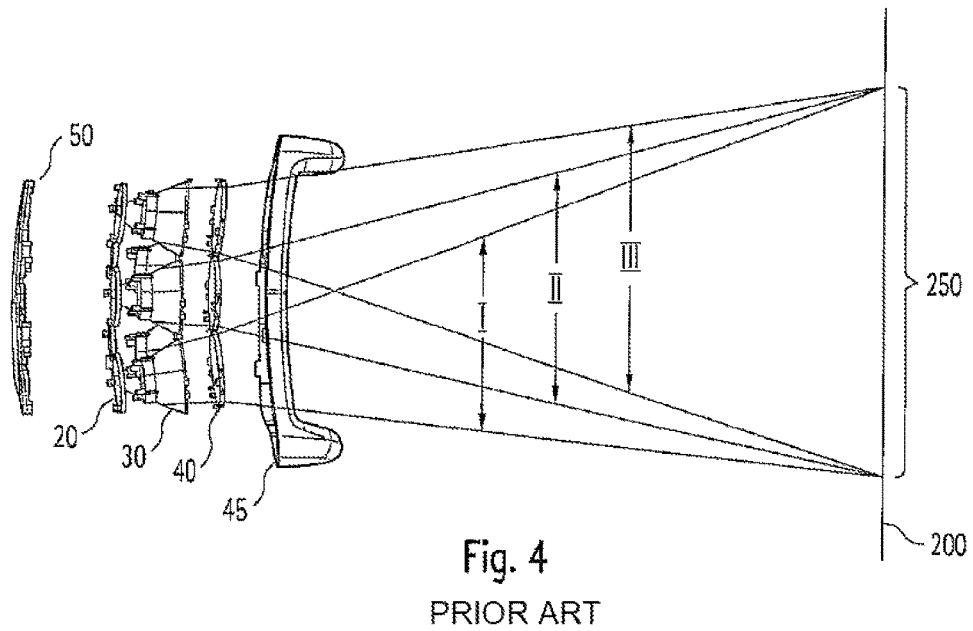

This superposing of the various bundles of rays of the illuminating units 10 is effected in this case also in a plane that is perpendicular to the representation according to FIG. 3, as is shown in FIG. 4. Here the superposing of the three illuminating units 10 arranged in the upper row is represented, whereby, once again, all three bundles of rays I, II and III are substantially identically superposed in the object plane 200 which, for example, is arranged at a spacing of 70 cm in front of the luminaire 100.

The previous explanatory remarks are also applicable, for example, to the luminaire already known from the state of the art. However, it has become evident that here the ultimately achievable illumination can be optimised still further.

A first problem consists, for example, in the fact that in the marginal region of the field of light 250 a relatively intense fall-off in brightness takes place. This leads to very strong contrasts in the illumination, which may have a fatiguing effect for example on the dentist and/or the dental nurse. A further problem consists in the fact that a 100% exact superposition of the individual light bundles of the illuminating units 10 cannot be achieved, by reason of manufacturing tolerances and such like. A certain offset when generating the field of light 250 in the object plane 200 will inevitably exist, which is then ultimately perceived as a non-uniform illumination of the surgical field.

Figure 5:
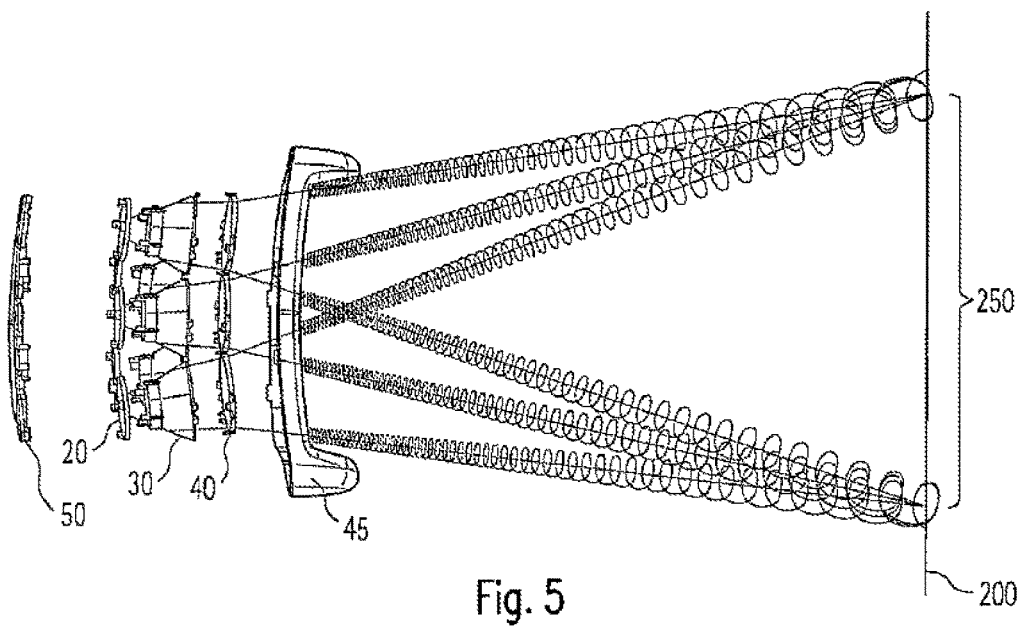
FIG. 5 is an overhead view of the emission of light in the case of the luminaire according to one embodiment of the invention.

In order to avoid these problems, in accordance with the invention it is proposed to integrate a diffuser into the beam path of the emission of light. In the embodiment of a luminaire according to the invention as represented in FIG. 5 there is provision, to this end, to integrate the diffuser into the light-transmitting cover 45 of the luminaire. The representation shown in FIG. 5 corresponds in this connection to the representation shown in FIG. 4, though it has now been indicated schematically that by reason of the light-scattering properties of the cover 45 the individual bundles of rays are slightly widened. In comparison with the representation according to FIGS. 3 and 4, in which it was assumed that the cover 45 is constituted by a plane window, for example by a non-light-scattering window, by this means the marginal regions of the superposed light bundles are accordingly slightly enlarged. In this case it is a question of a merely weak scattering which is additionally included in the influence exerted on the emission of light. This slight scattering, however, now has the consequence that a slightly enlarged field of light 250 results which, however, by reason of the lowering of the contrasts or of the brightness gradient in the marginal region, is perceived as more uniformly and more agreeably illuminated. Furthermore, the reduced contrasts in the marginal region also have a less fatiguing effect on the activity of the eyes, for example of the dentist.

Figure 6:
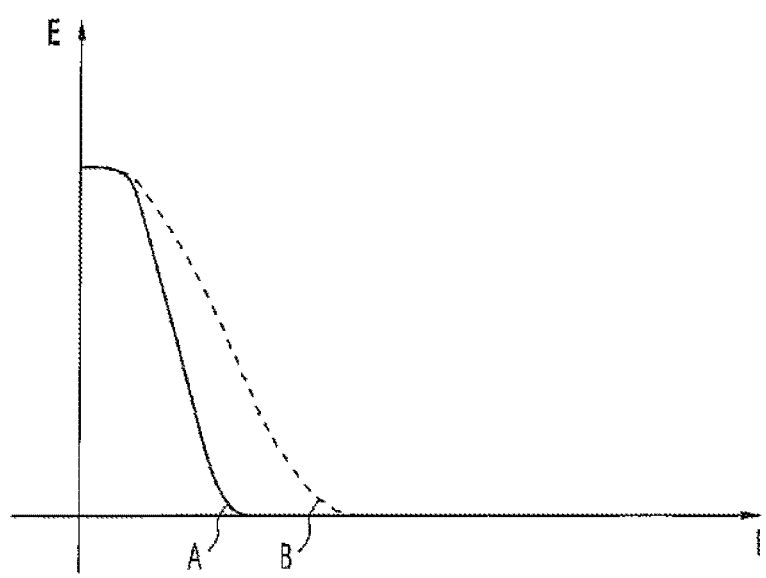
FIG. 6 is a graph comparing the drop in intensity in the marginal region of the illuminated field in the case of a luminaire according to the state of the art, such as illustrated in FIGS. 3 and 4, and the luminaire of FIG. 5.

This reduction of the brightness gradient is represented schematically in FIG. 6, which shows the fall-off in brightness in the marginal region of the field of light in the case of the luminaire according to the state of the art (curve A) and also, in comparison therewith, the fall-off in the case of the luminaire according to one embodiment of the invention (e.g., as illustrated in FIG. 5) (curve B). It is distinctly discernible that the marginal region in the case of the luminaire according to this embodiment of the invention is accordingly slightly "blurred". The has the result that slight deviations in the orientation of the various luminaire units, which, as already mentioned, are scarcely to be avoided anyway, are now no longer perceived as shadings in the marginal region of the field of light. However, by virtue of this measure not only is an improvements of the illumination situation in the marginal region of the field of light achieved, but additionally the effect is also obtained that a distinctly more uniform appearance results over the entire field of light.

One embodiment for realising the diffuser consists, as already mentioned, in integrating said diffuser into the cover 45. Since in the case of the cover 45 it is a question, as a rule, of a plastic part that is produced in an injection-moulding process, in this case there is the possibility of fashioning the appropriate tool for producing the cover already correspondingly, so that, for example, on the inside of the cover 45 facing towards the light-sources suitable light-scattering structures are formed. This accordingly represents a very economical and nevertheless efficient procedure in order to fashion the luminaires in the manner according to the invention.

In this connection it has turned out to be advantageous if the diffuser is realised with the aid of a holographic structure, for example a so-called µ-structure. This structure may be designed in such a manner that the light passing through it is circularly or elliptically polarised, whereby the diffuser, in spite of everything, has a high transmittance. The polarising of the light passing through in this case results in the additional advantageous effect that reflections, for example on the dental surface, are reduced, and accordingly there is a distinctly lower risk of dazzling the physician.

As an alternative to the proposed procedure, the diffuser could, however, also be, for example, a constituent of the second optical means 40. Also in this case there would be the possibility of providing the corresponding optical element, once again preferably produced in an injection-moulding process, already with the light-scattering properties.

Finally, there would also be the possibility of introducing the diffuser into the luminaire 100 as a separate structural element. In this case a corresponding flexible or rigid film could then find application, which is then preferably arranged between the second optical means 40 and the cover 45.

Lastly, the solution according to embodiments of the invention can accordingly be realised with the aid of measures that are relatively easy to carry out. In spite of everything, with the aid of these measures the emission of light of the luminaire is significantly improved. In this connection the advantages of the diffuser have an effect already on the emission of light of an individual illuminating unit. That is to say, a luminaire according to embodiments of the invention does not necessarily have to have a plurality of illuminating units, as is the case in the embodiment shown. Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

What is claimed is:

1. A medical luminaire for intraoral illumination of a surgical field, the medical luminaire comprising:
   a plurality of LEDs, each configured to generate a beam of light, and having
   at least one diverging lens positioned in a path of the beam of light configured to widen the beam of light to a field of light in an object plane, and
   a collimator positioned in the path of the beam of light between the LEDs and the at least one diverging lens, wherein the collimator is configured to transform the beam of light into a beam of collimated light, and wherein the at least one diverging lens is configured to widen the beam of light from the collimator and to form a virtual light source; and
   a light-transmitting injection-molded plastic cover including a plurality of light-scattering structures formed on an inside surface of the cover, wherein the cover is positioned in the path of the beam of light between the at least one diverging lens and the object plane, and wherein the light-scattering structures on the inside surface of the cover cause the cover to operate as a diffuser that lowers a contrast gradient in a marginal region of the field of light in the object plane, wherein the marginal region is where the field of light of each of the plurality of LEDs do not perfectly coincide in the object plane.

2. The medical luminaire according to claim 1, wherein the diffuser is configured to transmit only circularly or elliptically polarised light.

3. The medical luminaire according to claim 2, wherein the diffuser is configured to scatter light.

4. The medical luminaire according to claim 2, wherein the diffuser comprises a holographic structure.

5. The medical luminaire according to claim 1, further comprising a plurality of diverging lenses.

6. The medical luminaire according to claim 5, wherein each of the plurality of lenses is configured to project a bundle of rays passing through it onto the field of light in the object plane.

7. The medical luminaire according to claim 5, wherein each of the plurality of lenses is configured to deflect a bundle of rays passing through it in such a manner that the bundles of rays projected onto the object plane produce, in their totality, the field of light.

8. The medical luminaire according to claim 1, wherein the diffuser comprises a film and is arranged in the path of the beam of light.

9. The medical luminaire according to claim 1, wherein the diffuser is formed on an optically active surface of an optical means or on a cover plate of the luminaire.

10. The medical luminaire according to claim 1, further comprising an LED array.

11. A medical luminaire for intraoral illumination of a surgical field, the medical luminaire comprising:
    a plurality of illuminating units, each illuminating unit including a LED light source, a collimator and at least one diverging lens, each illuminating unit generating a field of light in an object plane, wherein each illuminating unit of the plurality of illuminating units is coupled to a common carrier at different locations on the common carrier and oriented so that the fields of light generated by each illuminating unit of the plurality of illuminating units substantially coincide at the object plane; and
    a common diffuser for the plurality of illuminating units positioned downstream of the plurality of illuminating units, wherein the common diffuser is configured to widen the field of light generated by each illuminating unit and to lower a contrast gradient in a marginal region of each field of light, wherein the marginal region is where the field of light of each illuminating unit do not perfectly coincide in the object plane.

12. The medical luminaire according to claim 11, further comprising a light-transmitting cover, wherein the common diffusor is integrated into the light-transmitting cover of the medical luminaire.

13. The medical luminaire according to claim 12, wherein the light transmitting cover is an injection-molded plastic part and includes light-scattering structures formed on an inside surface of the light-transmitting cover.

* * * * *